United States Patent [19]

Hagen

[11] Patent Number: 5,277,696
[45] Date of Patent: Jan. 11, 1994

[54] MEDICAL HIGH FREQUENCY COAGULATION INSTRUMENT

[75] Inventor: Alfred Hagen, Tuttlingen, Fed. Rep. of Germany

[73] Assignee: Delma elektro- und medizinische Apparatebau Gesellschaft mbH, Tuttlingen, Fed. Rep. of Germany

[21] Appl. No.: 959,875

[22] Filed: Oct. 13, 1992

[30] Foreign Application Priority Data

Nov. 19, 1991 [DE] Fed. Rep. of Germany ....... 4138115

[51] Int. Cl.$^5$ ................................................ A61B 17/36
[52] U.S. Cl. ....................................... 606/49; 606/50; 606/41; 606/45; 128/4
[58] Field of Search ........................ 606/27, 28, 35, 29, 606/39, 40, 45, 47, 48, 49, 50, 46; 604/21, 187; 137/4, 9, 10; 128/4 A

[56] References Cited

U.S. PATENT DOCUMENTS

| | | | |
|---|---|---|---|
| 3,838,242 | 9/1974 | Goucher | 606/27 |
| 4,181,131 | 1/1980 | Ogiu | 606/47 |
| 4,581,021 | 4/1986 | Landau et al. | 604/187 |
| 4,787,891 | 11/1988 | Levin et al. | 604/187 |
| 4,800,869 | 1/1989 | Nakajima | 128/4 A |

Primary Examiner—Stephen C. Pellegrino
Assistant Examiner—S. Harris
Attorney, Agent, or Firm—Townsend and Townsend Khourie and Crew

[57] ABSTRACT

A radio frequency coagulation instrument has two concentric tubular feedlines (15, 16) with coagulation electrodes (13, 14) at their end. The tubular feedlines (15, 16) are simultaneously used to supply the radio frequency current to the coagulation electrode (13, 14) and for the supply and removal of a flushing liquid. Moreover, the passage (19) formed within the tubular feedline (16) which serves for the removal of flushing liquid, and which is expediently connected to a vacuum source, can be used independently of the supply of flushing liquid to suck away not only flushing liquid but also, or alternatively, blood, body fluids, secretions and pieces of body tissue.

15 Claims, 2 Drawing Sheets

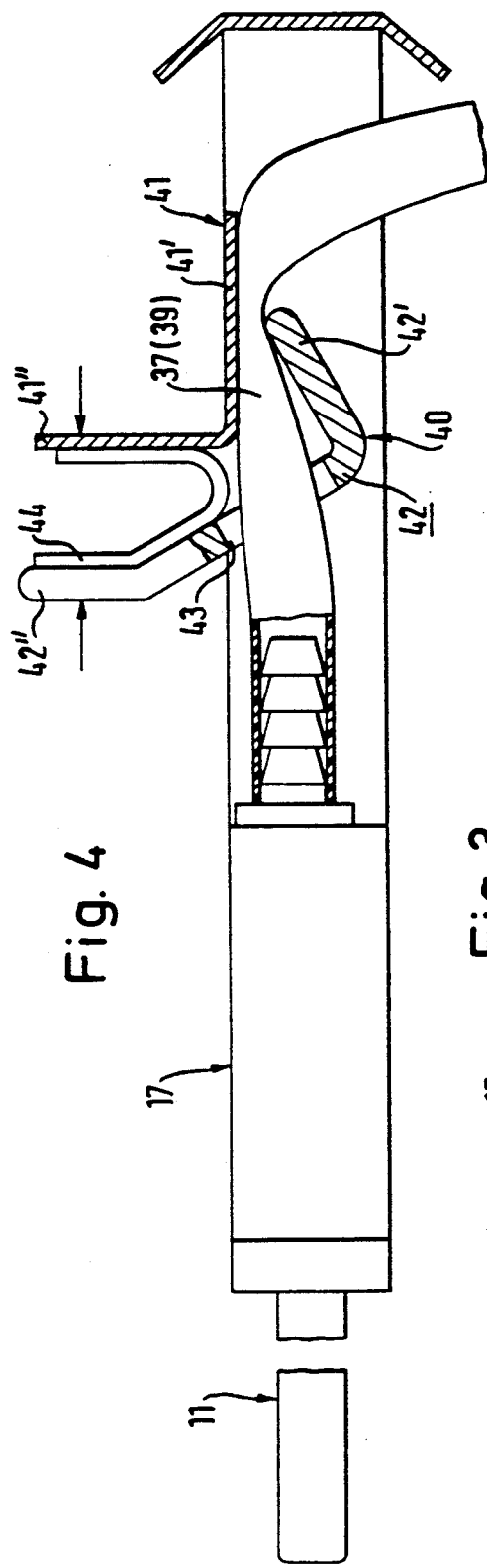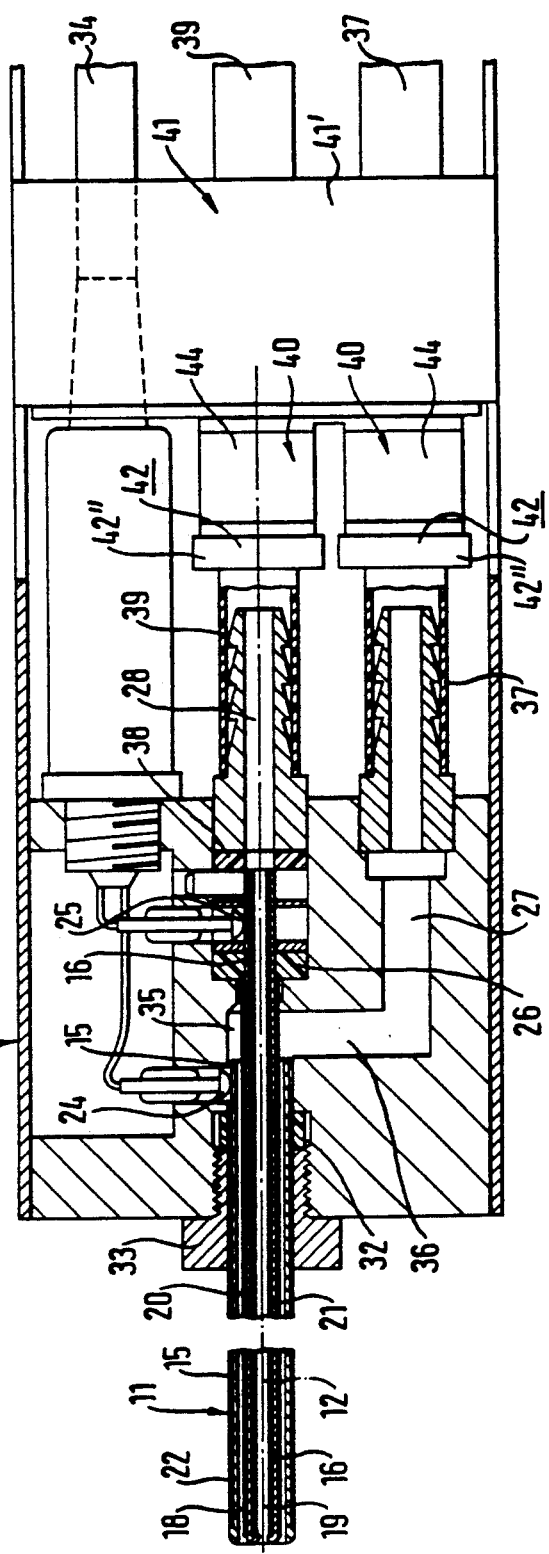

MEDICAL HIGH FREQUENCY COAGULATION INSTRUMENT

BACKGROUND OF THE INVENTION

The invention relates to a medical radio high frequency coagulation instrument. More specifically, the invention relates to a medical radio frequency coagulation instrument with a preferably circular cylindrical instrument shaft which has, at the proximal end, two electrically conductive coagulation ring electrodes which are arranged inside one another and preferably concentric to one another and to the shaft axis. Electrically conductive mutually insulated tubular feedlines extend rearwardly from the electrically conductive coagulation ring electrodes, are preferably formed in one piece therewith, and also, are preferably arranged concentric to one another and to the shaft axis, with the distal end of the tubular feedlines being connected to a connection piece for the supply of the required radio frequency current.

In a known electro-surgical treatment instrument of this kind (DE-OS 41 22 219) the two coagulation electrodes cooperate with a cutting electrode arranged concentrically to them. The coagulation electrodes are placed in use onto the tissue or vessel to be coagulated, whereupon the radio frequency coagulation current is switched on by means of a control device for a period until the desired coagulation has been carried out through the current flow between the two coagulation electrodes.

SUMMARY OF THE INVENTION

The aim of the invention is to provide an improved high frequency coagulation instrument. In particular, this instrument should make it possible to remove tissue parts and/or liquids which are set free in the region of the operation.

In order to satisfy this object, the present invention provides a medical high frequency coagulation instrument of the initially named kind, but characterized in that axial liquid supply and removal channels are provided between the walls of the two tubular feedlines and in the interior of the inner tubular feedline.

One advantageous further development of the invention is characterized in that an electrical insulation layer is provided between the walls of the tubular feedlines in addition to the liquid supply and removal channels. This, an insulating layer, preferably in the form shrinkable hose, is advantageously provided on the outer side of the inner tubular feedline. In addition, an insulating layer, preferably in the form of a plastic tube, is usefully provided on the inner side of the inner tubular feedline. Finally, an insulating layer, preferably in the form of a shrinkable hose, is advantageously provided on the outer side of the outer tubular feedline. The insulating layers should terminate in the region of the coagulation electrodes so that the front and side portions of the electrodes are exposed to the tissue during an operation.

Radial spacers are usefully provided between the walls of the tubular feedlines and/or their insulating layers in such a design and arrangement that they do not prevent the axial flow of liquid.

In addition, like invention exploits the intermediate space between the two tubular feedlines and the inner space of the inner tubular feedline in order to direct a flushing liquid to the site of the operation and to suck up liquid there simultaneously with the coagulation process. This liquid can also be supplied prior to the coagulation process or Expressed otherwise, the walls of the liquid channels are exploited to additionally guide a coagulation current to the proximal end of the instrument shaft.

Within a connection block, the electrical tubular feedlines are connected in a suitable manner with the electrical contacts to which the coagulation current can be supplied via a suitable radio frequency apparatus. Furthermore, the liquid supply and removal channels are connected within the connection block in a suitable manner with liquid supply and discharge lines. A particularly advantageous embodiment for such a connection is characterized in that the inner tubular feedline in the connection part projects rearwardly beyond the outer tubular feedline, and in that electrical contacts are applied radially from the outside to the de-insulated tubular feedlines and are connectable to the high frequency source, with the liquid supply and removal channels being connected at axially differing positions, which are sealed relative to one another, to the liquid supply and discharge lines.

For reasons of cleaning, and also for repair or replacement, a releasable arrangement of the instrument shaft at the connection black is preferred.

In order to set the liquid supply and/or discharge into operation in the simplest manner, and also to be able to interrupt it again, there is provided, in accordance with a preferred embodiment of the invention, an arrangement in which at least one valve, and preferably two valves, are present in the connection block for the control of liquid supply and/or discharge.

A preferred embodiment is characterized in that the valve has a fixed abutment and a cranked clamping lever which has a clamping limb and an actuating limb provided with an aperture for the passage of a hose, the actuating limb being connected via a spreading spring with one limb of the abutment which presses the clamping limb against a further limb of the abutment in such a way that the hose which passes through it is clamped off.

The invention will be described in the following by way of example and with reference to the drawing in which are shown:

BRIEF DESCRIPTION OF THE DRAWINGS

FIG. 3 shows a corresponding section through the instrument of the invention, with a scale reduced relative to FIGS. 1 and 2 having been selected, and FIG. 4 shows a partly sectioned side view of the subject of FIG. 3.

DESCRIPTION OF THE PREFERRED EMBODIMENTS

Figures 1, 2:
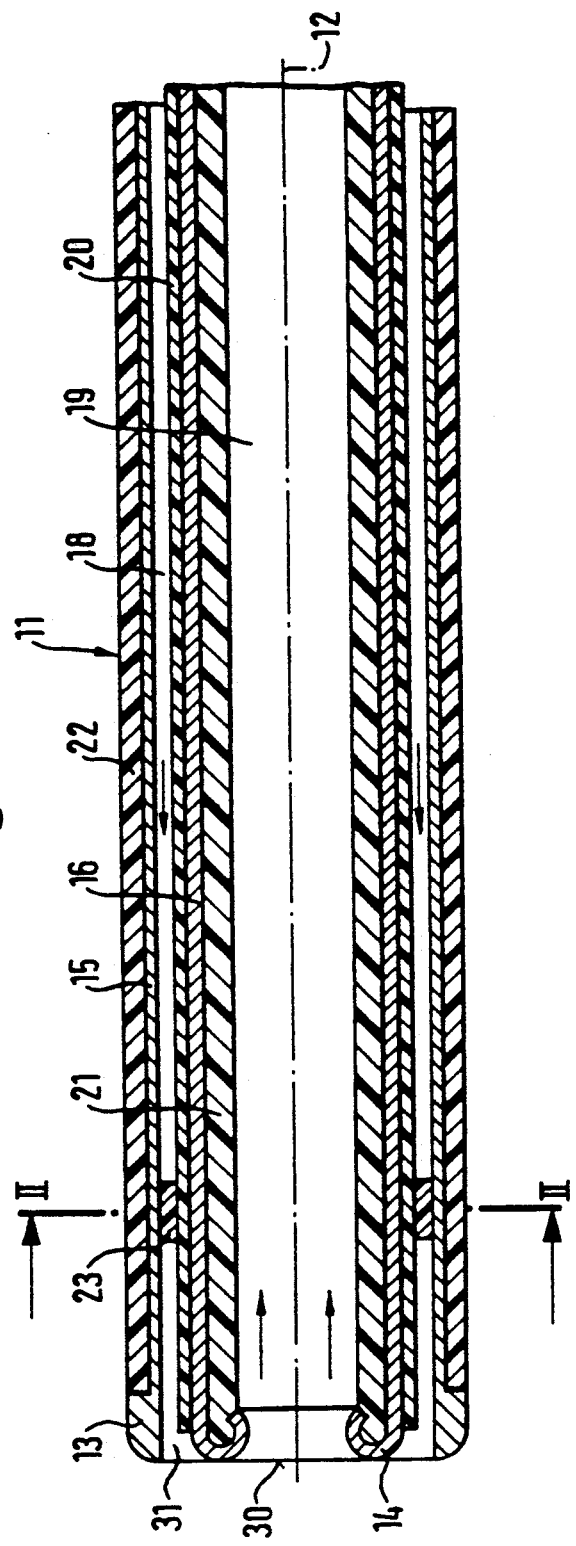
FIG. 1 shows an axial section through the instrument shaft of a coagulation instrument in accordance with the invention in the proximal zone.
FIG. 2 shows a section in accordance with the line II—II in FIG. 1.

In accordance with FIG. 1, two ring-like coagulation electrodes 13, 14 are arranged concentric to one another at the front end of a ring-cylindrical instrument shaft 11, having an axis 12. The electrodes are rounded in the illustrated manner and, in this embodiment, are flush with one another at the proximal end 30.

Towards the rear, the electrodes 13, 14 each merge their respective tubular feedlines 15, 16 which are concentric to them and to the shaft axis 12, and which are covered with insulated shrinkable hoses 22 and 20 respectively. The inner tubular feedline 16 is, moreover, covered over at its inner side by an insulating hose 21. It is important that the insulations 20, 21, 22 only extend up to the ring electrodes 13, 14 but not also beyond the latter. The metallic surfaces of the ring electrodes 13, 14 must be exposed at the front and optionally also somewhat at the side so that their action can be realized.

Between the walls of the tubular feedlines 15, 16, or the shrinkable hose 20 which covers over the inner tubular feedline 16, there is located a ring-cylindrical liquid supply channel 18 or passage, through which a suitable flushing liquid can be directed in the direction of the arrow to the annular exit opening 31 at the proximal end 30.

Spacers 23, which are preferably insulating, can be arranged between the inner wall of the tubular feedline 15 and the outer wall of the shrinkable hose 20. The spacers 23 and ensure a defined spacing of the two tube arrangement and avoid mechanical oscillations between them. In accordance with FIG. 2, there are, for example, four such spacers 23 arranged and distributed around the periphery, with the spacers 23 taking up such a small portion in the peripheral direction that the axial flow passage between them is hindered as little as possible. Such spacer arrangements can be provided at several positions distributed over the length of the instrument shaft 11.

The diameter of the inner tubular feedline 16 and of the plastic hose 21 applied thereto, is large enough to provide a central liquid extraction or removal channel 19 through which the liquid can be sucked away out of the operating zone in the direction of the arrow. It will be appreciated that the extraction channel or passage 19 not only serves to suck away a flushing liquid supplied through the passage 18, but can also be operated independently of the supply of flushing liquid to suck away blood, body fluids, secretions and pieces of tissue, etc. For this purpose, a source of suction or vacuum can be connected to the extraction channel or passage 19 to generate a suction effect for the sucking away of said blood, body fluids, secretions and pieces of tissue and/or said flushing liquid supplied via the passage 18 (or otherwise).

In accordance with FIG. 3, the rear end of the instrument shaft 11 is designed such the inner tubular feedline 16 projects axially rearwardly significantly beyond the outer tubular feedline 15. The so formed end of the instrument shaft Il is pushed into a bore 32 complementary thereto of a connection block 17 and is secured there, for example, by means of a suitably designed clamping screw 33.

The insulating layers 22 and 20, respectively, are removed in the rear region so that radial contacts 24, 25 provided there in the connection block 17 can enter into electrical connection with the tubular feedlines 15, 16. The radio frequency current required for coagulation can be supplied to the contacts 14, 25 via a cable 34 which is connected to a non-illustrated radio frequency apparatus.

Around the projecting end of the tubular feedline 16 which projects rearwardly beyond the tubular feedline 15, there is provided a ring-like liquid infeed chamber 35 which is connected via radial channel 36 to a liquid supply line 27 to which a suitable flushing liquid is supplied from the outside, for example, via a hose 37.

At its rear end, the annular space 35 is sealed via a ring seal 26 relative to the area where the contact 25 to the tubular feedline 16 is applied.

The rear end of the tubular feedline 16 lies axially against a ring seal 38 and is axially aligned with a liquid discharge line 28 which is connected in the illustrated manner with a liquid discharge hose 39.

In the rear region of the connection block 17, where the hoses 37, 39 extend to the lines 27, 28, two valves 40 are built-in in accordance with FIG. 4, which are very simple to manufacture, and to operate, and with which the liquid supply and discharge can be individually regulated. Each valve 40 has a fixed angular abutment 41 and a pivotable cranked clamping lever 42. The cranked clamping lever 42 has a clamping limb 42' and an angled actuating limb 42" in which a bore 43 is provided for the passage of the associated hose 37 or 39, respectively. Above this there extends, between the actuating limb 42" and an upwardly angled part 41" of the abutment 41, a V-shaped spreading spring 44 which is welded to the actuating limb 42" and to the part 41"'. In the relaxed state, in accordance with FIGS. 3 and 4, the spreading spring 44 pivots the clamping limb 42 upwardly so that the hose 37 or 39 is pressed against the limb 41' of the abutment 41 lying parallel to it and is clamped off in the illustrated manner so that the passage of liquid is interrupted.

When a force is manually exerted with the fingers between the upper abutment limb 41" and the actuating limb 42" in the direction of the two arrows shown in FIG. 4, the spreading spring 44 is compressed and the clamping off of the hose 37 or 39, respectively, is thereby cancelled in that the clamping limb 42' is pivoted downwardly.

In this manner the flushing liquid supplied or the liquid flow which is led away through the hose 37 or 39 can be interrupted in the simplest manner or can be directed to the instrument shaft 11. Hinges or other complicated valve arrangements are not necessary for this purpose.

What is claimed is:

1. A medical instrument for coagulating a tissue with a high frequency current comprising:

an instrument shaft forming a proximal end for placement near the tissue, a distal end and a shaft axis, the shaft including at least two electrically conductive coagulation ring electrodes at the proximal end such that the electrodes can be brought into contact with the tissue during an operation, the electrodes being arranged inside one another and parallel to the shaft axis;

at least two electrically conductive mutually insulated tubular feedlines extending from the electrodes toward the distal end of the shaft, the electrodes merging with the two tubular feedlines close to the proximal end such that each electrode forms one piece with its respective tubular feedline, one of the tubular feedlines being arranged inside and spaced from the other one of the tubular feedlines and parallel to the shaft axis such that there is an inner tubular feedline and an outer tubular feedline;

a connection block for the high frequency current, the connection block being electrically connected to the tubular feedlines at the distal end of the shaft;

first and second liquid flow channels extending parallel to the shaft axis, the first channel being formed between the inner tubular feedline and the outer tubular feedline, and the second channel being formed inside the inner tubular feedline, wherein one of the channels is a liquid supply channel through which a liquid can flow to the tissue being coagulated and another one of the channels is a liquid removal channel through which liquid can be withdrawn from the tissue.

2. A coagulation instrument in accordance with claim 1, further comprising a first electrical insulation layer, parallel to the shaft axis, disposed between the inner tubular feedline and the outer tubular feedline.

3. A coagulation instrument in accordance with claim 2, wherein the first electrical insulation layer is a shrinkable hose.

4. A coagulation instrument in accordance with claim 1, further comprising a second insulation layer, parallel to the shaft axis, disposed between the inner tubular feedline and the axial liquid removal channel.

5. A coagulation instrument in accordance with claim 4, wherein the second insulation layer is a plastic tube.

6. A coagulation instrument in accordance with claim 1, further comprising a third insulation layer, parallel to the shaft axis, disposed outward from he outer tubular feedline.

7. A coagulation instrument in accordance with claim 1, further comprising at least two spacers provided within the first liquid channel, the spacers ensuring that a distance between the inner tubular feedline and the outer tubular feedline remains fixed.

8. A coagulation instrument in accordance with claim 1, wherein the electrodes each have a front portion at the proximal end of the shaft, the front portion extending further towards the proximal end of the shaft than the first electrical insulation layer, the second insulation layer and the third insulation layer such that the front portion of the electrodes is exposed to the tissue.

9. A coagulation instrument in accordance with claim 1, wherein the tubular feedlines project into the connection block, the inner tubular feedline projecting further into the connection block than the outer tubular feedline, the tubular feedlines projecting further into the connection block than the first electrical insulation layer and the third insulation layer, and electrical contacts are applied to portions of the tubular feedlines projecting past the insulation layers.

10. A coagulation instrument in accordance with claim 9, including a high frequency source providing the high frequency current connected to the electrical contacts.

11. A coagulation instrument in accordance with claim 10, wherein the first and second channels project into the connection block, and including liquid supply and discharge lines in fluid communication with the channels such that the channels are sealed relative to one another.

12. A coagulation instrument in accordance with claim 1, wherein the electrodes forming the instrument shaft are releasably connected to the connection block.

13. A coagulation instrument in accordance with claim 1 further comprising at least one valve housed within the connection block for controlling a supply of the liquid to the liquid supply channel and a removal of the liquid from the liquid removal channel.

14. A coagulation instrument in accordance with claim 1, further comprising suction means coupled to the liquid removal channel for withdrawing a solid or liquid object from the tissue through the liquid removal channel.

15. A medical instrument for coagulating a tissue with a high frequency current comprising:
an instrument shaft forming a proximal end for placement near the tissue, a distal end and a shaft axis, the shaft including at least two electrically conductive coagulation ring electrodes at the proximal end such that the electrodes can be brought into contact with the tissue during an operation, the electrodes being arranged inside one another and parallel to the shaft axis;
at least two electrically conductive mutually insulated tubular feedlines extending from the electrodes toward the distal end of the shaft, the electrodes merging with the two tubular feedlines close to the proximal end such that each electrode forms one piece with its respective tubular feedline, one of the tubular feedlines being arranged inside and spaced from the other one of the tubular feedlines and parallel to the shaft axis such that there is an inner tubular feedline and an outer tubular feedline;
a connection block for the high frequency current, the connection block being electrically connected to the tubular feedlines at the distal end of the shaft;
first and second liquid flow channels extending parallel to the shaft axis, the first channel being formed between the inner tubular feedline and the outer tubular feedline, and the second channel being formed inside the inner tubular feedline, wherein one of the channels is a liquid supply channel through which a liquid can flow to the tissue being coagulated and another one of the channels is a liquid removal channel through which the liquid can be withdrawn from the tissue; and
at least one valve housed within the connection block for controlling a supply of the liquid to the liquid supply channel and a removal of the liquid from the liquid removal channels, the valve comprising:
a fixed abutment having first and second limbs and a movable clamping lever having a clamping limb and an actuating limb provided with an aperture, a spreading spring connected with the first limb and the actuating limb;
a hose passing through the aperture, the first limb so that the hose is disposed between the clamping limb and the second limb of the abutment such that the hose can be clamped off by moving the clamping lever against a force exerted by the spreading spring.

* * * * *